(12) United States Patent
Zhao et al.

(10) Patent No.: US 11,547,989 B2
(45) Date of Patent: Jan. 10, 2023

(54) CORED ROUND TRILOBE SHAPED CATALYST FOR PRODUCING MALEIC ANHYDRIDE

(71) Applicant: Huntsman Petrochemical LLC, The Woodlands, TX (US)

(72) Inventors: Chunli Zhao, The Woodlands, TX (US); Bennie Albert Horrell, Jr., The Woodlands, TX (US); William S. Frazee, The Woodlands, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 57 days.

(21) Appl. No.: 16/966,638

(22) PCT Filed: Feb. 5, 2019

(86) PCT No.: PCT/US2019/016599
§ 371 (c)(1),
(2) Date: Jul. 31, 2020

(87) PCT Pub. No.: WO2019/156953
PCT Pub. Date: Aug. 15, 2019

(65) Prior Publication Data
US 2021/0031177 A1  Feb. 4, 2021

Related U.S. Application Data

(60) Provisional application No. 62/629,385, filed on Feb. 12, 2018.

(51) Int. Cl.
| | | |
|---|---|---|
| *C07D 307/60* | (2006.01) | |
| *B01J 35/02* | (2006.01) | |
| *B01J 27/198* | (2006.01) | |
| *B01J 37/00* | (2006.01) | |
| *B01J 37/08* | (2006.01) | |
| *B01J 35/10* | (2006.01) | |

(52) U.S. Cl.
CPC ........... *B01J 35/026* (2013.01); *B01J 27/198* (2013.01); *B01J 35/023* (2013.01); *B01J 35/1014* (2013.01); *B01J 35/1038* (2013.01); *B01J 37/0009* (2013.01); *B01J 37/08* (2013.01); *C07D 307/60* (2013.01); *B01J 2531/56* (2013.01)

(58) Field of Classification Search
CPC .... B01J 35/026; B01J 35/023; B01J 35/1038; B01J 35/1014; B01J 37/0009; B01J 37/08; B01J 37/088; B01J 37/0018; B01J 37/14; B01J 37/16; B01J 27/198; B01J 23/002; B01J 23/22; B01J 2531/56; C07D 307/60
USPC ................. 502/209, 527.19, 527.23, 527.24; 549/256, 257, 258, 259, 261, 262
See application file for complete search history.

(56) References Cited

U.S. PATENT DOCUMENTS

| | | |
|---|---|---|
| 4,283,307 A | 8/1981 | Barone |
| 4,656,157 A | 4/1987 | Hofmann et al. |
| 5,168,090 A | 12/1992 | Ebner et al. |
| 6,005,121 A | 12/1999 | Ebner et al. |
| 6,812,351 B2 | 11/2004 | Weiguny et al. |
| 8,048,820 B2 | 11/2011 | Brandstadter et al. |
| 9,138,729 B2 | 9/2015 | Dobner et al. |
| 2013/0338378 A1 | 12/2013 | Reitzmann et al. |

FOREIGN PATENT DOCUMENTS

| | | |
|---|---|---|
| EP | 0220933 A1 | 5/1987 |

OTHER PUBLICATIONS

International Search Report and Written Opinion received in corresponding PCT Application No. PCT/US2019/016599 completed Mar. 19, 2019 and dated Apr. 22, 2019.

*Primary Examiner* — Elizabeth D Wood
(74) *Attorney, Agent, or Firm* — Huntsman Petrochemical LLC; Aleece Hayes

(57) ABSTRACT

The present disclosure provides an improved shaped catalyst containing catalytic material comprised of mixed oxides of vanadium and phosphorus and using such shaped catalysts for the production of maleic anhydride.

20 Claims, 5 Drawing Sheets

CORED ROUND TRILOBE SHAPED CATALYST FOR PRODUCING MALEIC ANHYDRIDE

CROSS-REFERENCE TO RELATED APPLICATIONS

This application is the National Phase of International Application PCT/US2019/016599 filed Feb. 5, 2019 which designated the U.S. and which claims priority to U.S. Provisional App. Ser. No. 62/629,385 filed Feb. 12, 2018. The noted applications are incorporated herein by reference.

STATEMENT REGARDING FEDERALLY SPONSORED RESEARCH OR DEVELOPMENT

Not applicable.

FIELD OF THE INVENTION

The present disclosure generally relates to shaped catalysts comprising oxides of vanadium and phosphorus which may be used in the production of maleic anhydride.

BACKGROUND

Maleic anhydride is a well-known and versatile material for the manufacture of unsaturated polyester resins, chemical intermediates (e.g. butanediol and tetrahydrofuran), pharmaceuticals and agrochemicals. It is produced by partial oxidation of aromatic or non-aromatic hydrocarbons in the gas phase and in the presence of a catalyst. The oxidation reaction may be carried out in a fixed, fluidized, or riser bed reactor.

Catalysts based on vanadium and phosphorus oxides ("VPO catalysts") have been developed for use in the oxidation reaction described above. In particular, VPO catalysts particularly well suited to catalyze the oxidation reactor are those in which the valence of the vanadium is less than +5, usually between about +3.8 and about +4.5.

Conventional methods of preparing these catalysts generally involve reducing a pentavalent vanadium compound, and combining the same with a phosphorus compound, and promoter element compounds if desired, to form a catalyst oxide precursor. The catalyst oxide precursor is then recovered and converted to active catalytic material.

It is generally known that by selecting varied geometrical cross-sectional configurations, formed catalytic particles may be designed to offer shorter diffusion paths for reactants and/or products which may be desirable in reactions like those described above. Additionally, catalytic particle configuration has been employed in the past to reduce the pressure drop encountered across a packed catalyst bed, and/or to reduce catalyst loss due to breakage, abrasion or crushing during storage, handling, sizing or when severe process conditions are encountered.

Therefore, the prior art has suggested many shapes, including rods, cylinders, spheres, spools, etc., of various sizes, dimensions and proportions for VPO catalysts including:

U.S. Pat. No. 4,283,307 which discloses a VPO catalyst in the shape of a small cylinder with a hole therethrough and where the height and diameter of the cylinder are substantially the same;

U.S. Pat. No. 4,656,157 which discloses a VPO catalyst that is in the shape of a hollow cylinder with end faces curved such that the radius of curvature is from 0.4 to 5 times the external diameter;

U.S. Pat. No. 5,168,090 which discloses a VPO catalyst having a solid geometric form (for e.g. cylinder, cube, cone, sphere) with at least one void space disposed in its external surface;

U.S. Pat. No. 6,812,351 which discloses a VPO catalyst having an essentially hollow cylindrical body and a ratio of height to the diameter of the continuous hole of not more than 1.5 and a ratio of geometric surface area to geometric volume of at least 2 $mm^{-1}$;

U.S. Pat. No. 9,138,729 which discloses a VPO catalyst having an essentially cylindrical body with at least two internal holes parallel to the axis of the cylindrical body;

EP 0220933A1 which discloses a VPO catalyst having a quadrilobe cross-sectional shape; and U.S. Pat. No. 8,048,820 which discloses a VPO catalyst having a traditional trilobe cross-sectional shape where each lobe is provided with a continuous internal hole.

Although each of the shapes above provide VPO catalysts with appreciable activity and selectivity in the preparation of maleic anhydride, it is desirable to provide improved shaped catalysts which maximize productivity, minimize pressure drop in the reaction system and have sufficient mechanical stability.

SUMMARY

According to one aspect, the present disclosure provides a shaped catalyst for producing maleic anhydride. The shaped catalyst comprises:

a) a catalytic material comprising mixed oxides of vanadium and phosphorus;
b) a hollow core; and
c) a first end, a second end and a wall disposed between the first end and the second end, the wall comprising a height and a plurality of crenellations running along the height of the wall to form a plurality of lobes wherein each lobe has a corner defined by a lobe radius.

In a further aspect, there is provided a method of making the shaped catalyst above by reacting a vanadium-containing compound and a phosphorus-containing compound in an alcoholic medium to produce a VPO catalyst precursor, shaping the VPO catalyst precursor to form the shaped catalyst and activating the shaped catalyst by calcination.

In still another aspect, there is provided a process for producing maleic anhydride by reacting a hydrocarbon having at least four carbons in a straight chain or cyclic ring with a molecular oxygen-containing gas in the presence of the shaped catalyst.

DETAILED DESCRIPTION

The following terms shall have the following meanings.

If appearing herein, the term "comprising" and derivatives thereof are not intended to exclude the presence of any additional component, step or procedure, whether or not the same is disclosed herein. In contrast, the term, "consisting essentially of" if appearing herein, excludes from the scope of any succeeding recitation any other component, step or procedure, except those that are not essential to operability and the term "consisting of", if used, excludes any component, step or procedure not specifically delineated or listed. The term "or", unless stated otherwise, refers to the listed members individually as well as in any combination.

The articles "a" and "an" are used herein to refer to one or to more than one (i.e. to at least one) of the grammatical objects of the article. By way of example, "a hydrocarbon" means one hydrocarbon or more than one hydrocarbon. The phrases "in one aspect", "according to one aspect" and the like generally mean the particular feature, structure, or characteristic following the phrase is included in at least one aspect of the present disclosure, and may be included in more than one aspect of the present disclosure. Importantly, such phrases do not necessarily refer to the same aspect. If the specification states a component or feature "may", "can", "could", or "might" be included or have a characteristic, that particular component or feature is not required to be included or have the characteristic.

As used herein, the term "hollow core" refers to one central vacancy within an object, which is completely surrounded by the material of the object.

Figure 6:
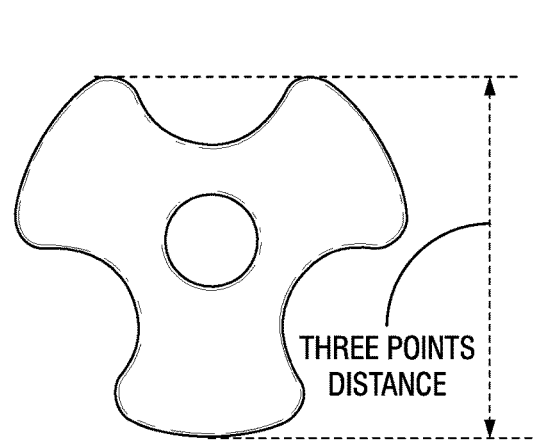
FIG. 6 is a top-elevational view of a shaped catalyst according to the present disclosure depicting the three points of contact distance.

The term "three points of contact distance" refers to the distance between i) a first imaginary line tangential to adjacent corners of two lobes and ii) a second imaginary line parallel to the first imaginary line and tangential to the shaped catalyst as depicted in FIG. 6.

Figure 7:
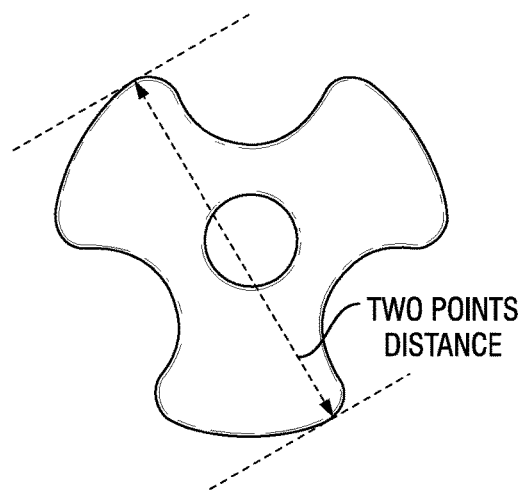
FIG. 7 is a top-elevational view of a shaped catalyst according to the present disclosure depicting the two points of contact distance.

The term "two points of contact distance" refers to the distance between i) a first imaginary line tangential to a corner of a first lobe and ii) a second imaginary line parallel to the first imaginary line and tangential to a corner of a second lobe as depicted in FIG. 7.

The term "conversion" means the ratio of the moles of hydrocarbon feedstock reacted to the moles of hydrocarbon feedstock introduced into the reactor multiplied by 100 with the term expressed as mole percent.

The term "yield" means the ratio of the moles of maleic anhydride obtained to the moles of hydrocarbon feedstock introduced into the reactor multiplied by 100 with the term expressed as mole percent.

The term "selectivity" means the ratio of the moles of maleic anhydride obtained to the moles of hydrocarbon feedstock reacted or converted multiplied by 100 with the term expressed as mole percent.

The term "space velocity" or "gas hourly space velocity" or "GHSV" means the hourly volume of gaseous feed expressed in cubic centimeters ($cm^3$) at 20° C. and atmospheric pressure, divided by the catalyst bulk volume, expressed as $cm^3/cm^3$/hour or $hr^{-1}$.

The term "productivity" means the weight of maleic anhydride produced per unit volume/reactor (e.g., kilograms maleic anhydride/hr). An increased productivity means that more maleic anhydride can be synthesized per unit time.

The term "BET surface area" is a standardized measure to indicate the specific surface area of a material as measured by the standard BET nitrogen test according to ASTM D-3663-03.

The term "calcination" generally embraces one or more gas and/or thermal treatment steps of a catalyst precursor. The term "active" catalyst thus refers to a catalyst that has been transformed from a catalyst precursor by treatment with one or more gas and/or thermal treatment steps.

The present disclosure provides a novel and improved shaped catalyst for producing maleic anhydride by the partial oxidation of a hydrocarbon in the vapor phase with molecular oxygen or a molecular oxygen-containing gas. The shaped catalyst of the present disclosure generally comprises a catalytic material comprising mixed oxides of vanadium and phosphorus, a hollow core, a first end, a second end and a wall disposed between the first end and the second end, the wall comprising a height and a plurality of crenellations running along the height of the wall to form a plurality of lobes. Each lobe has a corner that is defined by a lobe radius.

As a result of the above described novel shape, it is possible to take advantage of the crenellations to provide improved access of the hydrocarbon reactants to the catalyst interior and improved egress of the maleic anhydride product from the catalyst interior. Furthermore, because the lobes include corners defined by the lobe radius, the void space is relatively smaller as compared to conventional lobe shaped catalysts. Accordingly, the possibility of interlock between shaped catalysts of the present disclosure is reduced thereby allowing filling of the reactor to be simpler and more reproducible when forming a homogenous bed. Moreover, the combination of the crenellations and hollow core in the shaped catalyst of the present disclosure has surprisingly been found to reduce the longest diffusion path for the shaped catalyst significantly more than expected.

The shaped catalyst in accordance with the present disclosure has also been surprisingly found to be easily produced and provides for reduced pressure drop across a packed catalyst bed and reduced catalyst loss due to breakage, crushing and handling, sizing, regeneration or under other severe process conditions as compared to conventional lobed shaped structures.

Moreover, it will be apparent to those skilled in the art that a shaped catalyst must possess sufficient mechanical resistance or physical strength to withstand handling, transportation from the source of manufacture to the reactor in which it is to be used, and charging into the reactor. In addition, the shaped catalyst must be able to support its own weight in the reactor. Or stated differently, the shaped catalyst must possess mechanical resistance sufficient to substantially maintain the structural integrity of the shaped catalyst under handling and use conditions. If the shape has insufficient mechanical resistance, crushing can result. This, in turn, results in adverse economic consequences such as increased pressure drop and decreased reactant gas flow rates, increased costs for production due to yield losses to fines and broken pieces, and less efficient reactor operation due to hot spots in the catalyst bed.

In general, sufficient mechanical resistance as determined by side crush strength measurements—the amount of pressure required to break or crush the shaped structure—exists for shapes exhibiting a side crush strength of from 4.45 newtons (N) to 222.4 N (1 lb to 50 lb), preferably from 13.3 N to 133.5 N (3 lb to 30 lb). Or stated differently, the mechanical resistance of the shaped catalyst of the present disclosure is sufficient to substantially maintain the structural integrity thereof, while at the same time is not excessive to the point that the porosity is reduced to a value such that the movement of reactant hydrocarbon gas molecules into and maleic product out of the shaped catalyst is inhibited.

Thus, as compared to conventional lobe shaped catalysts, the shaped catalyst of the present disclosure has surprisingly been found to exhibit improved catalytic performance (i.e. having an improvement in at least one catalytic property such as, but not limited to, hydrocarbon throughput over the catalyst, reduced pressure drop, conversion, selectivity, yield, space time, productivity, loading characteristics or operability) during production of maleic anhydride.

Figure 1:
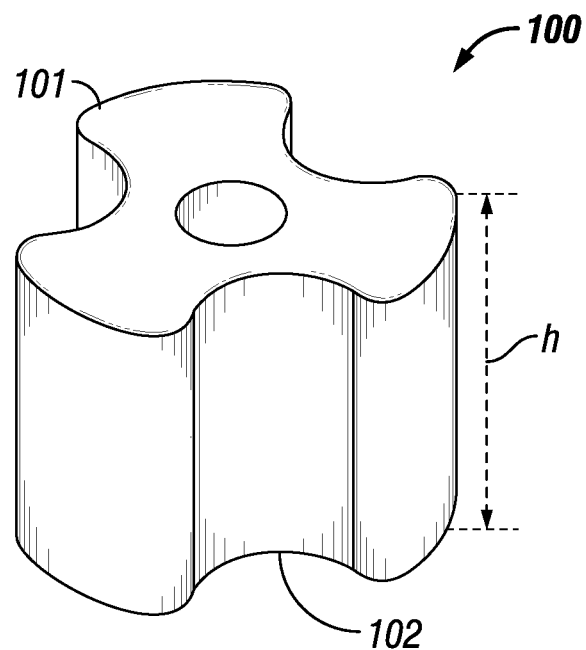
FIG. 1 is a perspective view of a shaped catalyst according to an aspect of the present disclosure.

As shown in FIG. 1, the shaped catalyst 100 of the present disclosure has a general shape different from a normal hollow cylindrical shape. The shaped catalyst generally has a hollow core, a first end, a second end and a wall disposed between the first end and the second end, the wall comprising a height and a plurality of crenellations running along the height to form a plurality of lobes where each lobe has a corner defined by a lobe radius. According to one aspect, the wall has three crenellations to form three lobes. In other aspects, the wall may have more than three crenellations, for example, four crenellations to form four lobes, or five crenellations to form five lobes, or even six crenellations to form six lobes.

Each crenellation may be a recess, pocket or channel forming a concave depression in the shaped catalyst. The crenellations can therefore take various forms, including circular arcs, although other forms may be used such as square, rectangular, V-shaped etc. In one particular aspect, the crenellations are circular arcs.

The shaped catalyst can further be described by various parameters. The parameters mentioned below are in each case the mean values for the shaped catalyst. This applies particularly in the case of deviations from the ideal geometry.

As described above, the shaped catalyst has a wall comprising a height h as shown in FIG. 1. In one aspect, the height h ranges from 1 mm to 20 mm, in other aspects from 2 mm to 15 mm, and in other aspects from 3 mm to 10 mm, and in even other aspects from 4 mm to 8 mm.

The shaped catalyst also has a first end 101 and a second end 102. The first end and second end may be circular or oval in cross-section having an outer diameter $d_1$. In another particular aspect, the first end and the second end are circular in cross section. In still another aspect, the first end and second end have an outer diameter $d_1$ ranging from 3 mm to 10 mm, or in other aspects from 5 mm to 9 mm, or even in other aspects from 6 mm to 8 mm.

Figure 2A:
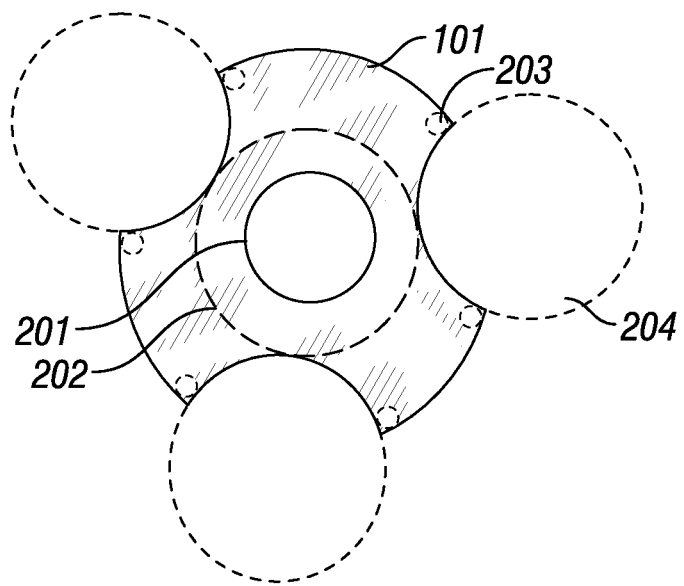
FIG. 2a is a top-elevational view of a shaped catalyst according to the present disclosure.
Figure 2B:
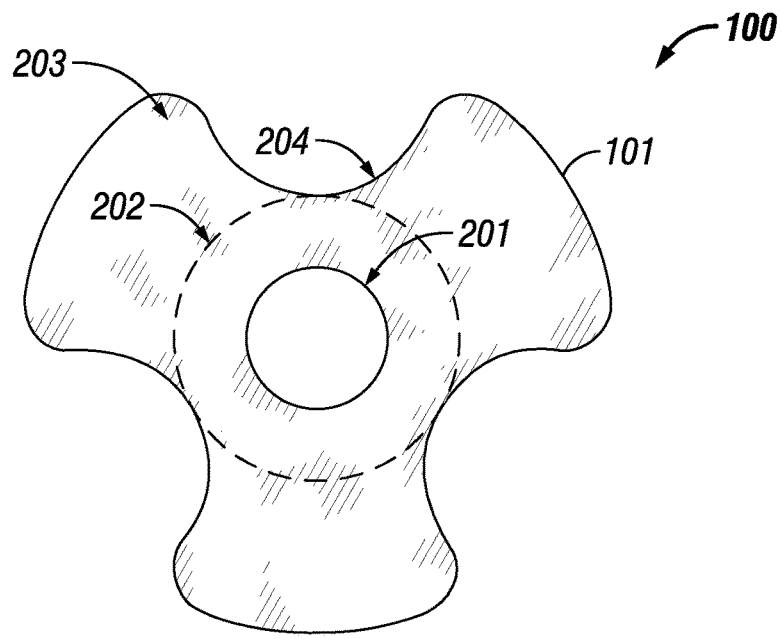
FIG. 2b is a top-elevational view of a shaped catalyst according to the present disclosure.
Figure 2C:
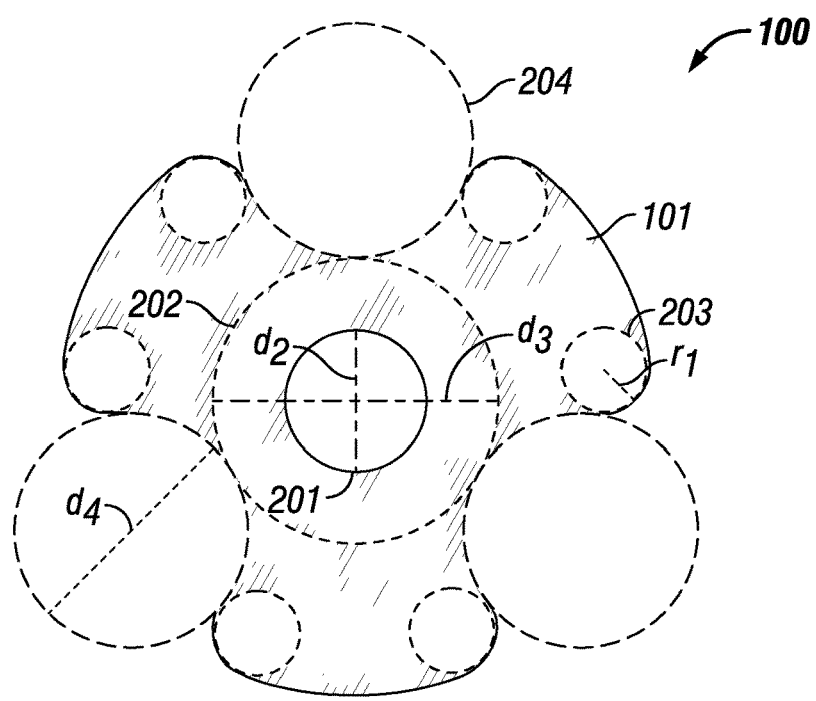
FIG. 2c is a top-elevational view of a shaped catalyst with illustration according to the present disclosure.

As shown in FIGS. 2a, 2b and 2c, the shaped catalyst also has a hollow core (or one internal hole) 201. The hollow core is continuous going from the first end to the second end and may be circular, oval or an ellipsoid in cross section, although in further aspects other geometric shapes may also be used, such as polygonal (for e.g. triangular, square, rectangular or hexagonal in cross section). According to one aspect, the hollow core is circular in cross section. In another aspect, the hollow core has a core diameter $d_2$ ranging from 0.5 mm to 4 mm, or in other aspects from 1 mm to 3 mm or in further aspects from 1.5 mm to 2.25 mm. In another aspect, the shaped catalyst has an outer diameter $d_1$ that is circular in cross section. In a further aspect, the outer diameter $d_1$ may range from about 3.2 mm to about 8 mm or from about 4 mm to about 7.2 mm.

The shaped catalyst can further be described by an inner crenellation feature 202 resulting from connecting the innermost points of the crenellations.

In one aspect, the inner crenellation feature is a circle as shown in FIGS. 2a, 2b and 2c. In another aspect the inner crenellation feature has a diameter $d_3$ ranging from 1.5 mm to 5 mm, or in other aspects from 2 mm to 4.5 mm or even in other aspects from 3 mm to 4 mm.

Figure 3:
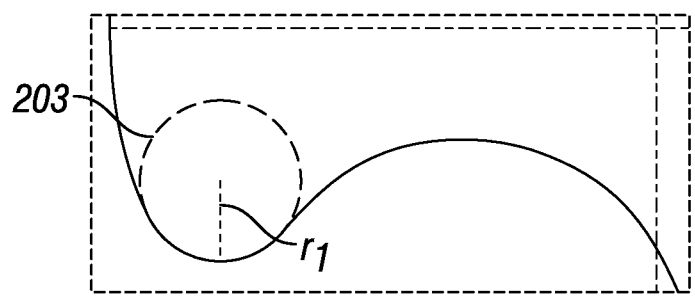
FIG. 3 is a top-elevational view of a magnified region of a shaped catalyst according to the present disclosure with its lobe radius more clearly defined.
Figure 4A:
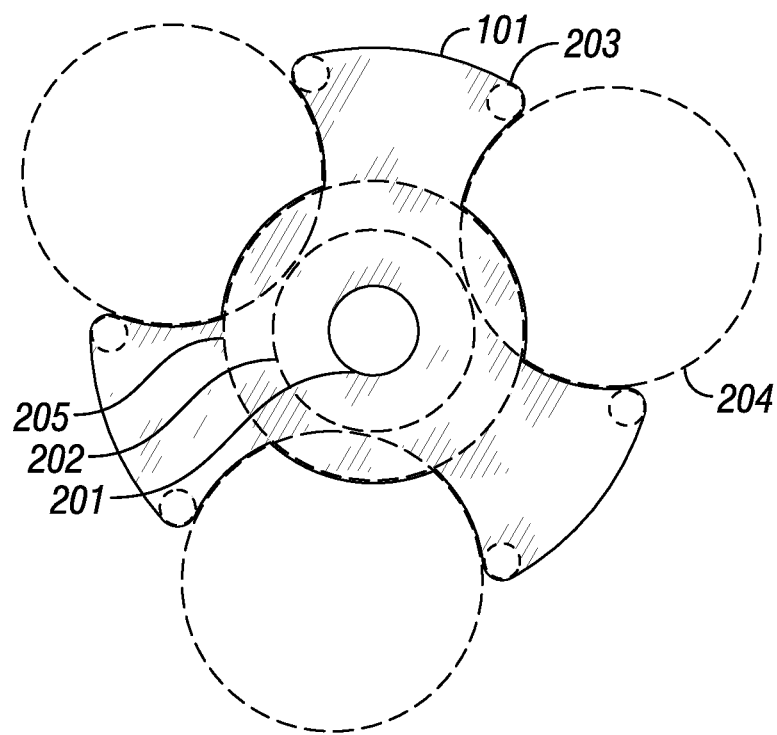
FIGS. 4a, 4b, 5a and 5b are top-elevational views of a shaped catalyst according to a further aspect of the present disclosure.
Figure 4B:
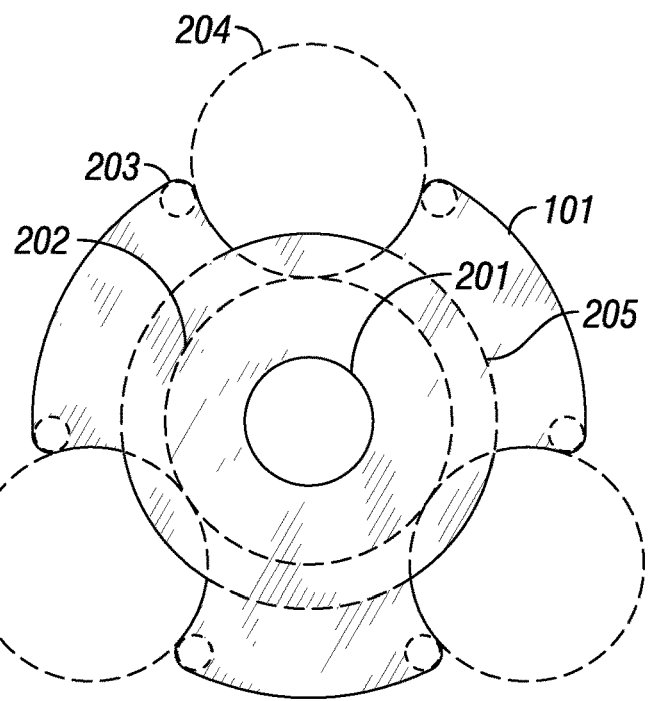

The plurality of lobes for the shaped catalyst have corners 203 that have a shape defined by a lobe radius $r_1$ as shown in FIGS. 2a and 3. According to one aspect, a corner of a lobe is rounded and has a lobe radius $r_1$ ranging from 0.25 mm to 1 mm, or in other aspects from 0.375 mm to 0.75 mm or even in other aspects from 0.5 mm to 0.7 mm.

As shown in FIG. 2a, the shaped catalyst can further be described by an outer crenellation feature 204 connecting the innermost points and projecting edges of a crenellation as shown in FIG. 2a. In one aspect, the outer crenellation feature is a circle. In another aspect, the outer crenellation feature has a diameter $d_4$ ranging from 1.5 mm to 4 mm, or in other aspects from 2 mm to 3.5 mm, or even in other aspects from 2.5 mm to 3.3 mm.

FIG. 2b is an alternative depiction of the shaped catalyst 100 shown in FIG. 2a.

FIG. 2c is a top elevational view of the first end 101 of the shaped catalyst 100 intended to illustrate the features described with respect to FIG. 2a in an alternative way. FIG. 2c shows the hollow core 201 having a diameter, $d_2$, and the inner crenellation feature 202 having a diameter, $d_3$. FIG. 2c further shows the corners 203 of the plurality of lobes for the shaped catalyst 100, which have a radius, $r_1$, as well as the outer crenellation feature 204 having a diameter, $d_4$.

FIG. 3 is a top elevational view of a magnified region of the corner 203 of the shaped catalyst with its lobe radius, $r_1$, more clearly defined.

In a further aspect, the shaped catalyst can further be described by various ratios. Thus, in one aspect, the ratio of the core diameter $d_2$ to the outer diameter $d_1$ for the shaped catalyst is at least 0.1, in other aspects at least 0.15 and in still other aspect at least 0.2. In another aspect, the ratio of the core diameter $d_2$ to the outer diameter $d_1$ for the shaped catalyst is less than 0.5, in other aspects less than 0.3 and in still other aspects less than 0.25. In yet another aspect, the ratio of the core diameter $d_2$ to the outer diameter $d_1$ for the shaped catalyst is between 0.1 and 0.4, in other aspects between 0.15 and 0.3 while in still other aspects between 0.2 and 0.25.

In another aspect, the ratio of the diameter $d_3$ of the inner crenellation feature connecting the innermost points of the crenellations to the outer diameter $d_1$ for the shaped catalyst is at least 0.3, and in other aspects at least 0.4. In yet another aspect, the ratio of the diameter $d_3$ of the inner crenellation feature connecting the innermost points of the crenellations to the outer diameter $d_1$ for the shaped catalyst is less than 0.6, and in other aspects less than 0.4. In still yet another aspect, the ratio of the diameter $d_3$ of the inner crenellation feature connecting the innermost points of the crenellations to the outer diameter $d_1$ for the shaped catalyst is between 0.35 and 0.6, in other aspects between 0.4 and 0.55 while in still other aspects between 0.45 and 0.5.

According to yet another aspect, the ratio of the lobe radius $r_1$ to the outer diameter $d_1$ for the shaped catalyst is at least 0.002 and in other aspects at least 0.07. In another aspect, the ratio of the lobe radius $r_1$ to the outer diameter $d_1$ for the shaped catalyst is less than 0.12 and in other aspects less than 0.09. In still yet another aspect, the ratio of the lobe radius $r_1$ to the outer diameter $d_1$ for the shaped catalyst is between 0.025 and 0.15, in other aspects between 0.05 and 0.125 while in still other aspects between 0.075 and 0.1.

In a further aspect, the ratio of the core diameter $d_2$ to the diameter $d_3$ of the inner crenellation feature connecting the innermost points of the crenellations for the shaped catalyst is at least 0.35 and in other aspects at least 0.45. In another aspect, the ratio of the core diameter $d_2$ to the diameter $d_3$ of the inner crenellation feature connecting the innermost points of the crenellations for the shaped catalyst is less than 0.6 and in other aspects less than 0.5. In yet another aspect, the ratio of the core diameter $d_2$ to the diameter $d_3$ of the inner crenellation feature connecting the innermost points of the crenellations for the shaped catalyst ranges between 0.3 and 0.7, in other aspects between 0.4 and 0.6 while in other aspects between 0.45 and 0.55.

In still another aspect, the ratio of the core diameter $d_2$ to the lobe radius $r_1$ for the shaped catalyst is at least 2 and in other aspects at least 2.5. In another aspect, the ratio of the core diameter $d_2$ to the lobe radius $r_1$ for the shaped catalyst is less than 3.5 and in other aspects less than 3.25. In yet another aspect, the ratio of the core diameter $d_2$ to the lobe radius $r_1$ for the shaped catalyst ranges between 2 and 4, in other aspects between 2.5 and 3.5 while in other aspects between 2.8 and 3.2.

According to one particular aspect, the shaped catalyst is shaped such that as the outer diameter $d_1$ increases or decreases, the ratios described above remain constant. Thus, in one aspect, the ratio of the core diameter $d_2$ to the outer diameter $d_1$ for the shaped catalyst is constant as $d_1$ increases or decreases. In another aspect, the ratio of the diameter $d_3$ of the inner crenellation feature connecting the innermost points of the crenellations to the outer diameter $d_1$ for the shaped catalyst is constant as $d_1$ increases or decreases. In still another aspect, the ratio of the lobe radius $r_1$ to the outer diameter $d_1$ for the shaped catalyst is constant as $d_1$ increases or decreases.

FIGS. 4a, 4b, 5a and 5b depict alternative aspects in which the shaped catalyst described above comprises an additional support crenellation feature 205 positioned between the outer diameter of the first end 101 and inner crenellation feature 202. In this particular aspect, the support crenellation feature is the diameter resulting from connecting the innermost points of the crenellations with the bottom portion of the crenellations being extended out as compared to those in FIG. 2a. The diameter for the support crenellation feature will vary depending on the desired amount of support to be provided to the shaped catalyst but will always be less than outer diameter of the first end and greater than the diameter of the inner crenellation feature.

Figure 5A:
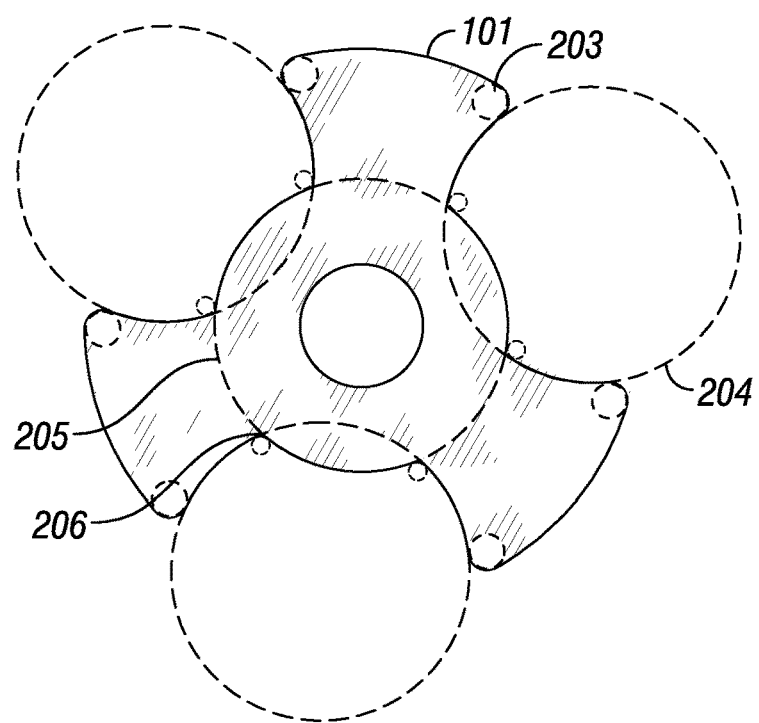
Figure 5B:
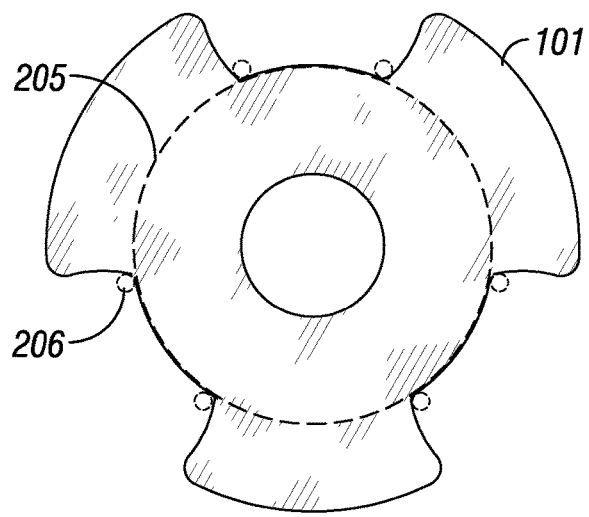

As shown in FIGS. 5a and 5b, the plurality of lobes for the shaped catalyst may have inner corners 206 that have a shape defined by an inner lobe radius $r_2$. In one aspect the inner corner is rounded. Again, the inner lobe radius $r_2$ will vary depending on the amount of support desired but will always be less than lobe radius $r_1$.

In still yet another aspect, the shaped catalyst can be described by a three points of contact distance as shown in FIG. 6. In one aspect, the shaped catalyst has a three points of contact distance which ranges between 4 mm and 8 mm, while in other aspects between 5.5 mm and 7.5 mm.

In still yet another aspect, the shaped catalyst can also be described by a two points of contact distance as shown in FIG. 7. In one aspect, the shaped catalyst will have a two points of contact distance which ranges between 5 mm and 10 mm, while in other aspects between 6 mm and 8 mm.

As described above, the shaped catalyst of the present disclosure exhibits a high side crush strength. In one aspect, the shaped catalyst of the present disclosure has a side crush strength greater than about 10 pounds. In other aspects, the shaped catalyst has a side crush strength greater than 15 pounds, or greater than 16 pounds, or greater than 17 pounds, or greater than 18, or greater than 19 or even greater than 20 pounds.

In still other aspects, the shaped catalyst according to the present disclosure may have a bulk density less than 0.75 kg/l or between 0.45 kg/l and 0.7 kg/l.

In still other aspects, the shaped catalyst of the present disclosure may have a BET surface area of about 10-100 $m^2/g$, or about 12-80 $m^2/g$ or about 15-50 $m^2/g$ or even about 20-35 $m^2/g$.

The shaped catalyst selected may be any kind of known active VPO catalyst used for organic selective oxidation, particularly maleic anhydride production. Thus in one aspect, the shaped catalyst may comprise 100% by weight catalytic material, based on the total weight of the shaped catalyst with no added inert diluents or supports. In other aspects, inert diluents or supports may be added to the shaped catalyst by the addition of the diluent or support. Such inert diluents or supports may include silica, alumina, alumina silica, titania, niobia, silicon carbide, and the like. Thus, in another aspect the shaped catalyst of the present disclosure may comprise at least 70% by weight catalytic material, based on the total weight of the shaped catalyst. In still another aspect the shaped catalyst may comprise at least 80% by weight catalytic material, based on the total weight of the shaped catalyst. In still yet another aspect, the shaped catalyst may comprise at least 90% by weight catalytic material, based on the total weight of the catalytic material.

Broadly described, the shaped catalyst can be prepared by reacting a vanadium-containing compound and a phosphorus-containing compound in an alcoholic medium to produce a VPO catalyst precursor comprising a precursor composition, shaping the VPO catalyst precursor to form a shaped catalyst and activating the shaped catalyst by calcination to convert a substantial fraction of the precursor composition to catalytic material.

More specifically, the VPO catalyst precursor may be prepared as described in U.S. Pat. Nos. 5,137,860 and 5,364,824 and WO 1997/012674, which are each incorporated by reference herein in their entirety and wherein the shaping is carried out according to the geometry of the various aspects.

In one aspect, the VPO catalyst precursor is prepared by introducing a substantially pentavalent vanadium-containing compound and a pentavalent phosphorus-containing compound into an alcohol medium to form a catalyst precursor slurry. The vanadium and phosphorus-containing compounds may be added simultaneously, or one after the other, in any convenient manner to the alcohol medium. After the vanadium and phosphorus-containing compounds are introduced into the alcohol medium to form the catalyst precursor slurry, reduction of at least a portion of the vanadium to a valence state of +4 is effected by reaction, preferably by heating the mixture, with stirring, if desired, until a blue solution or slurry is obtained. In general, heating the precursor slurry at the reflux temperature for a period of time ranging from about four (4) hours to about twenty (20) hours is sufficient.

The pentavalent vanadium-containing compounds that may be used as a source of vanadium include vanadium pentoxide or vanadium salts, such as ammonium metavanadate, vanadium oxytrihalides, and vanadium alkylcarboxylates. Among these compounds, vanadium pentoxide is preferred.

The pentavalent phosphorus-containing compounds useful as a source of phosphorus include phosphoric acid, phosphorus pentoxide, or phosphorus perhalides such as phosphorus pentachloride. Of these phosphorus compounds, phosphoric acid and phosphorus pentoxide are preferred.

The alcohols employed in the preparation of the VPO catalyst precursor are preferably anhydrous and, in some embodiments, capable of reducing at least a portion of the vanadium to a +4 valence state, either upon addition of the vanadium compound or upon mixing and heating. In addition, the alcohol may be a solvent for and relatively unreactive toward the phosphorus compound. In those instances where the VPO catalyst precursor is soluble in the alcohol medium, precursor precipitation may be easily induced by removal of a portion of the alcohol. Particular alcohols may include primary and secondary alcohols, such as methanol, ethanol, 1-propanol, 2-propanol, 1-butanol, 2-methyl-1-propanol (isobutyl alcohol), 2-butanol, 3-methyl-2-butanol, 2,2-dimethyl-1-propanol, 4-methyl-2-pentanol, and 1,2-ethanediol (ethylene glycol). Of these alcohols, isobutyl alcohol (IBA) is preferred.

As described above, optional promoter elements may be added. The promoter elements may be added as solids, suspension of solids, or solutions to the catalyst precursor slurry. Promoter compounds that may serve as sources of the promoter elements include metal halides, metal alkoxides, and metal carboxylates. Of these compounds, metal carboxylates are preferred. Suitable carboxylates for metal salts include formate, acetate, propionate, butyrate, isobutyrate, penitanoate, hexanoate, heptanoate, octanoate, nonanoate, decanoate, and 2-ethylhexanoate. Of these carboxylates, 2-ethylhexanoate is preferred.

The promoter elements may be added to the catalyst precursor slurry as metal 2-ethylhexanoates in solutions of alcohols, esters, aromatics, and alkanes. Of these solvents, isobutyl alcohol, isobutyl isobutyrate, decane, and mineral spirits constitute preferred but not limiting solvents of choice. In one aspect, the metal 2-ethylhexanoates are dissolved in suitable solvents in amounts of 20 percent by weight or less before they are added to the precursor slurry.

Reaction between the pentavalent vanadium-containing compounds and pentavalent phosphorus-containing compounds may be carried out at any suitable temperature. In one aspect, the reaction may be carried out at a temperature within a range of about 90° C. to about 120° C. and at a P/V ratio of 1.05 to 1.15.

During the course of carrying out the reaction, the VPO catalyst precursor forms and precipitates from the precursor slurry as a finely divided precipitate that may also contain the optional promoter elements. The VPO catalyst precursor may be recovered after cooling to below about 50° C. by conventional techniques well known to those skilled in the art, including filtration, centrifugation, and decantation.

The VPO catalyst precursor may then be dried at a relatively modest temperature of, for example, about 110° C. to about 150° C., and then subjected to "post dry" treatment (roasting) at a temperature in the range of about 200° C. to about 275° C.

The VPO catalyst precursor may be shaped by blending the VPO catalyst precursor with a shaped structure forming aid known in the art, such as graphite, starch, calcium stearate or stearic acid, along with any desirable inert filler material, and pressing or compacting in a mold (tableting press equipped with an appropriate die and punch) or by extrusion or casting in accordance with procedures known in the art. In one aspect, the compaction technique is preferred in that shaped structures exhibiting characterizing properties in accordance with the present disclosure are more readily obtained. The VPO catalyst precursor may be compressed into its final shape or form to a measured density of between about 1 g/cm³ to about 2 g/cm³, or about 1.20 g/cm³ to about 1.70 g/cm³, or between about 1.40 g/cm³ to about 1.60 g/cm³. In a similar manner, the absence of the employment of inert filler material may be preferred in some aspects since the partial oxidation reaction of hydrocarbon to maleic anhydride would be advantageously carried out in a manner which maximizes the amount of catalytic material contained in the specified volume of the reactor which thereby would maximize the amount of hydrocarbon converted in a single reactor pass.

In one particular aspect, the shaped catalyst can be produced from the VPO catalyst precursor by first mixing the VPO catalyst precursor with a binder or with a slip additive. The shaped catalyst can then be produced in a tablet press with a rotary table at the periphery of which several openings with a corresponding three lobed cross-section are disposed. The mixture is filled into this opening (female molds), and held from below by a punch of which, when the rotary table is rotated, three pins (for example) that are located at the points of the openings to be produced are pushed upwards. As the rotary table rotates further, a punch with a corresponding cross-section engages, and is provided with openings which the three pins penetrate when the upper punch is depressed. As the rotary table rotates further, the compressed shaped bodies are pressed out of the female molds after the lower punch has been withdrawn and the upper punch pushed further. The thus-formed shaped catalyst is then activated by calcination.

In one aspect, the shaped catalyst is activated by a series of steps in a controlled manner using a sequence of gas and thermal treatments (i.e. calcination): (1) an initial heat-up stage, (2) a rapid heat-up stage, and (3) a maintenance/finishing stage as described in U.S. Pat. No. 5,137,860 which is incorporated herein by reference in its entirety. The shaped catalyst produced corresponds to a composition comprising a catalytic material comprising mixed oxides of vanadium and phosphorus generally represented by the formula:

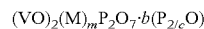

$$(VO)_2(M)_m P_2 O_7 \cdot b(P_{2/c}O)$$

where M is at least one promoter element selected from among elements of Groups IA, IB, IIA, IB, IIIA, IIIB, IVA, IVB, VA, VB, VIA, VIB, and VIIIA of the Periodic Table of the Elements, and mixtures thereof; m is a number from 0 to about 0.2; b is a number taken to provide a P/V atom ratio from about 1.0 to about 1.3; and c is a number representing the oxidation number of phosphorus and has a value of 5. The oxidation state of the vanadium is between about 4.0 and about 4.5, and in some aspects between about 4.06 and about 4.30. In one aspect, M is selected from chromium, nickel, magnesium, aluminum, silicon, tungsten, niobium, antimony, cesium and a mixture thereof.

Although the shaped catalyst, as represented by the above formula, is indicated as having a phosphorus-to-vanadium (phosphorus/vanadium or P/V) atom ratio from about 1.0 to about 1.3, in some aspects the ratio may be from about 1.0 to about 1.2, and in other aspects from about 1.05 to about 1.15. In another aspect the P/V atom ratio may range from a value as low as about 0.9 up to the stated value of about 1.3. The total atom ratio of promoter element-to-vanadium (promoter element/vanadium or MN), when a promoter element is present as a component of the shaped catalyst, may be in the range from about 0.0001 to about 0.2, or from about 0.0005 to about 0.1 or even from about 0.001 to about 0.05.

In the initial heat-up stage during calcination, the shaped catalyst may be heated in an atmosphere selected from among air, steam, inert gas, and mixtures thereof, at any convenient heat-up rate. In one aspect, the shaped catalyst may be heated to a temperature not to exceed the phase transformation initiation temperature, which may be about 300° C. In general, suitable temperatures for the initial heat-up stage range from about 200° C. to about 300° C., alternatively at a temperature from about 250° C. to about 275° C.

After the desired temperature has been achieved in the initial heat-up stage, the initially selected atmosphere (in the event it does not contain molecular oxygen and steam and/or has a different composition than that which is desired for the rapid heat-up stage) may be replaced by a molecular oxygen/steam-containing atmosphere, while maintaining the shaped catalyst at the temperature achieved in the initial heat-up stage. Such atmosphere optionally may contain an inert gas and, as such, may be conveniently represented by the formula:

$$(O2)_x(H2O)_y(IG)_z$$

where IG is an inert gas and x, y, and z represent mole % (or volume %) of the O2, H$_2$O, and IG components, respectively, in the molecular oxygen/steam-containing atmosphere; with x having a value greater than 0 mol %, but less than 100 mol %; y having a value greater than 0 mol %, but less than 100 mol %; and z having a value representing the balance of the molecular oxygen/steam-containing atmosphere. In one aspect, the atmosphere may contain at least a portion of molecular oxygen and water (as steam). The presence of the inert gas in such atmosphere, as indicated by the formula, is optional. Non-limiting examples of inert gases suitable for use in the molecular oxygen/steam-containing atmosphere include (molecular) nitrogen, helium, argon, and the like, with nitrogen generally being preferred.

Once the molecular oxygen/steam-containing atmosphere is provided, the shaped catalyst may be subjected to the rapid heat-up stage. In the rapid heat-up stage, the initial heat-up stage temperature is increased at a programmed rate of from about 2° C. per minute (° C./min) to about 12° C./min, or from about 4° C./min to about 8° C./min, to a value effective to eliminate or remove the water of hydration from the shaped catalyst structure. In general, a temperature from about 340° C. to about 450° C., alternatively at least about 350° C., alternatively from about 375° C. to about 425° C. may be suitable.

Following the rapid heat-up stage, the shaped catalyst may be subjected to the maintenance/finishing stage. In the maintenance/finishing stage, while the molecular oxygen/steam-containing atmosphere, is maintained, the temperature may be adjusted to a value greater than 350° C. but less than 550° C., or from about 375° C. to about 450° C. or even from about 400° C. to about 425° C. The adjusted temperature is then maintained, first in the molecular oxygen/steam-containing atmosphere for a time effective to provide a vanadium oxidation state of from about +4.0 to about +4.5 or simply from about 4.0 to about 4.5, and thereafter in a nonoxidizing, steam-containing atmosphere for a time effective to complete the shaped catalyst-to-active shaped catalyst transformation to yield a shaped catalyst corresponding to the composition comprising a catalytic material described above. In a manner similar to the molecular oxygen/steam-containing atmosphere, the nonoxidizing, steam-containing atmosphere may also optionally contain an inert gas, with nitrogen generally being the preferred inert gas.

In some aspects, the pore size inside of the shaped catalyst may be altered by a pore agent or a pore builder as described in U.S. Pat. Nos. 5,773,382 and 5,275,996, the contents of which are incorporated herein by reference.

Thus, according to one aspect, the shaped catalyst is mixed with a solvent-removable pore agent. The solvent-removable pore agent may be added to the shaped catalyst so that the mixture contains between about 6% and about 16%, or between about 8% and about 12% by weight of pore building agent based on the total weight of the shaped catalyst.

The solvent-removable pore agent that may be added includes, but is not limited to, a carboxylic acid, anhydride, ester, alcohols, polyols, carbohydrates, ketones, waxes, aromatic hydrocarbons (e.g., naphthalene), polymers (e.g., polystyrene, polyvinyl alcohol (PVA)), or combination thereof. In one aspect, the pore agent is a solid at the temperatures typically found during compaction and tableting and does not negatively chemically interact with the catalyst.

In one particular aspect, the solvent-removable pore agent is 1,1,1-tris(hydroxymethyl)ethane, trimethylolpropane, maleic anhydride, polyethylene oxide, or a combination thereof.

The solvent-removable pore agent may be removed by applying the appropriate solvent to the shaped catalyst. For example, the solvent-removable pore agent may be removed from the shaped catalyst by soaking and/or washing the catalyst at least once in the appropriate solvent for a certain period of time. The soaking period may depend on the particular solvent-removable pore agent/solvent combination but may generally range from about 2 hours to about 24 hours, alternatively from about 6 hours to about 8 hours, and alternatively from about 6 hours to about 24 hours. The amount of solvent that may be used may range from about a 1:2 to 2:1 weight ratio of solvent to shaped catalyst. The solvent-removable pore agent may also be removed by washing the shaped catalyst in a continuous stream of solvent. Again, the amount of washing may depend on the particular solvent-removable pore agent/solvent combination.

Any solvent that may solubilize the solvent-removable pore agent may be used. For example, the solvent may include one or more low molecular weight alcohols such as methanol or ethanol, a ketone such as acetone or methyl ethyl ketone, a supercritical CO$_2$, and/or esters such as ethyl acetate. For instance, one aspect includes a solvent comprising ethanol, methanol, methyl ethyl ketone, ethyl acetate, acetone, supercritical CO$_2$ or combination thereof.

After the solvent-removable pore agent is removed, it may be recovered from the solvent by any suitable means such as distillation or extraction.

The shaped catalyst may then be dried at a temperature range from about 45° C. to about 75° C. for a period of time ranging from about 1 hour to about 24 hours.

According to another aspect, the shaped catalyst may also be subjected to a series of contactings with one or more fluids. A series of contactings is herein understood to include a single contacting step and a combination of consecutive contacting steps which employ one or more fluids.

In one aspect, the fluid may comprise an organic solvent or mixture of organic solvents. In another aspect, each organic solvent has a dielectric constant within a range of about 5 to about 55, or within a range of about 10 to about 50. As used herein, the term "dielectric constant" is defined as a measure in the reduction of an electric field around a charged particle dissolved in the organic solvent, as compared to the electric field strength around the same particle in a vacuum. The value of the dielectric constant will depend on the temperature under which it is measured. Here, the dielectric constant of the organic solvent refers to the dielectric constant as measured at room temperature or a temperature of between 20° C. to 25° C.

Examples of organic solvents suitable for use include, but are not limited to, methanol, ethanol, n-propanol, n-butanol, isopropanol, isobutanol, acetonitrile, acetone, methyl ethyl ketone, DMF (N,N-dimethylformamide), Dimethyl sulfoxide, tetrafuran, ethylene glycol, propylene glycol, diethylene glycol, dipropylene glycol, 1,4-butanediol, glycerin and a mixture thereof.

Eligibly, the fluid comprises for the greater part the organic solvent or mixture of organic solvents. Thus, the organic solvent content of the fluid in one aspect is at least 90% by weight, or at least 95% by weight, or even at least 99% by weight, in particular, at least 99.9% by weight, or even at least 99.99% by weight relative to the weight of the fluid. In one aspect, the fluid consists of an organic solvent or mixture organic solvents.

In another aspect, the fluid may further comprise relative small quantities of other components, including, but not limited to, water, other organic matter, or inorganic matter.

The extent and type of contacting may be carried out in a continuous fashion or it may be carried out in a batch type of operation. There may be one contacting, but the number of contactings may also be two or three or more, for example up to five or ten. The contacting of the shaped catalyst may be static or slow-motion relative to the fluid(s).

The quantity of fluid used in the contactings relative to the quantity of shaped catalyst may be enough to cover the shaped catalyst. The contacting may be carried out at any suitable temperature range, preferably within a range from room temperature (i.e. 20°-25° C.) to about 100° C. above the boiling point of the fluid, and more preferably from room temperature to the boiling point of the fluid. The contacting may be conducted in any pressure range, preferably from atmospheric pressure to 5 bars, or from atmospheric pressure to 3 bars or even at around 2 bars.

Contacting time may vary depending on the treatment conditions. The contacting time may be from a few minutes to a few weeks. Thus, in one aspect, the contacting time may range from a period of about 5 minutes to about 2 days. In another aspect, the contacting time may range from a period of about 0.5 hours to about 12 hours.

After contacting the shaped catalyst, it may be desirable to perform a drying step. Drying of the contacted shaped catalyst may be performed at a certain temperature range under certain atmosphere. In one aspect, drying may be carried out at a temperature ranging from about room temperature (i.e. ° C. to 25° C.) to a temperature sufficient to remove the fluid from the shaped catalyst, for example, 300° C. In another aspect, the temperature to remove the fluid from the shaped catalyst may be about 200° C. The temperature during drying may be held constant or varied over time. The drying may be carried out under a pressure range from about atmospheric pressure to vacuum with 10 mbar or with 50 mbar. The atmosphere may comprise air or inert gases or a mixture of air and inert gases. The inert gases may include nitrogen, helium, argon, carbon oxides, and mixtures thereof. In one aspect, the atmosphere comprises air or nitrogen or a mixture thereof. The length of time of the drying step may vary from about 0.1 hour to a week or from about 0.5 hours to 3 days, or from about 1 hour to 12 hours depending on drying conditions.

The shaped catalyst is useful in a variety of reactors to convert aromatic and non-aromatic hydrocarbons to maleic anhydride. The shaped catalyst of the present disclosure can be used in both fixed-bed reactors and in fluidized-bed or transport-bed reactors.

Thus, in another aspect, the present disclosure provides a process for preparing maleic anhydride which process comprises reacting a hydrocarbon having at least four (4) carbons in a straight chain or cyclic ring with a molecular oxygen-containing gas in the presence of the shaped catalyst of this disclosure. The process may be carried out as a batch process; however, in another aspect, the process is carried out continuously. In one aspect, the process is a gas phase process, wherein a gaseous feed comprising the reactants is contacted with the solid shaped catalyst. The shaped catalyst is present in the form of a packed or fixed bed.

In yet another aspect, the shaped catalyst is used in tube-shell fixed-bed (tubular) with heat exchanger-type reactors. The tubes of such reactors may be constructed of iron, stainless steel, carbon steel, nickel, and/or glass and may vary in diameter from about 0.635 cm (0.25 inch) to about 5.08 cm (2 inches) and in length from about 15.24 cm (6 inches) to about 762 cm (25 feet) or more. It is desirable to have the surfaces of the reactors at relatively constant temperatures, and some medium to conduct heat from the reactors. Non-limiting examples of such media include Woods metal, molten sulfur, mercury, molten lead, and eutectic salt baths. A metal block reactor, whereby the metal surrounding the tube acts as a temperature regulating body, may also be used.

The hydrocarbon having at least four carbons in a straight chain or cyclic ring as used herein refers to a hydrocarbon containing not less than four carbon atoms in either a straight chain or in a cyclic ring. The hydrocarbon may be saturated, unsaturated, cyclic or aromatic. Typically, the hydrocarbon contains four to ten carbon atoms. Thus, in addition to n-butane, other saturated hydrocarbons include the pentanes, the hexanes, the heptanes, the octanes, the nonanes, the decanes, and mixtures of any of these, with or without n-butane, so long as a hydrocarbon having at least four carbon atoms in a straight chain is present in the saturated hydrocarbon molecule.

The hydrocarbon having at least four carbons in a straight chain also includes unsaturated hydrocarbons. Unsaturated hydrocarbons suitable for use include the butenes such as 1-butene and 2-butene, 1,3-butadiene, the pentenes, the hexenes, the heptenes, the octenes, the nonenes, the decenes, and mixtures of any of these, with or without the butenes, again, so long as the requisite hydrocarbon chain having at least four carbon atoms in a straight chain is present in the molecule.

In another embodiment, the hydrocarbon having at least four carbons in a cyclic ring is a cyclic hydrocarbon, for example, cyclopentane and cyclopentene, or an aromatic hydrocarbon, such as benzene.

According to one aspect, the hydrocarbon having at least four carbons in a straight chain or cyclic ring is selected from n-butane as the saturated hydrocarbon, 1-butene or 2-butene as the unsaturated hydrocarbons, and benzene as the aromatic hydrocarbons and a mixture thereof, with n-butane being most preferred of all feedstocks. It will be noted that the aforementioned feedstocks may not be pure substances but may be technical grade hydrocarbons. Moreover, a mixture of hydrocarbons having at least four carbon atoms in a straight chain or cyclic ring may also be used. The use of n-butane and an n-butane-containing mixture of hydrocarbon gases and liquids is particularly preferred especially those produced in refinery streams.

The reaction to convert a hydrocarbon to maleic anhydride may include contacting the hydrocarbon having at least four carbons in a straight chain (or in a cyclic structure) admixed with a molecular oxygen-containing gas (including molecular oxygen), such as air, synthetic air, molecular oxygen-enriched air, or "pure" oxygen (i.e. oxygen originating from air fractionation) and the shaped catalyst at elevated temperatures. In addition to the hydrocarbon and molecular oxygen-containing gas, other gases such as nitrogen and steam may be present or added to the reactant feed stream. In one aspect, the hydrocarbon may be admixed with the molecular oxygen-containing gas, for instance air, at a concentration of from about one (1) mole percent to about ten (10) mole percent hydrocarbon and contacted with the shaped catalyst at a space velocity of about 100 $hr^{-1}$ to about 4,000 $hr^{-1}$ and a temperature between about 300° C. and about 600° C., or at a space velocity of about 1,000 $hr^{-1}$ to 3,000 $hr^{-1}$ and at a temperature of about 325° C. to about 450° C. to provide an excellent yield and selectivity to maleic anhydride.

The reaction may be conducted at atmospheric, super atmospheric, or subatmospheric pressure. In one aspect, the reaction may be conducted at or near atmospheric pressure. Generally, pressures of from about 1.013×10-2 kPa-gauge (14.7 psig, 1 atmosphere) to about 3.45×10-2 kPa-gauge (50 psig) may be conveniently employed.

The principal product from the oxidation of the aforementioned suitable feedstock is maleic anhydride, although small amounts of citraconic anhydride (methyl maleic anhydride) may also be produced when the feedstock is a hydrocarbon containing more than four carbon atoms. The maleic anhydride produced by using the shaped catalyst may be recovered by any suitable means. For example, maleic anhydride may be recovered by direct condensation or by absorption in suitable media with subsequent separation and purification of the maleic anhydride.

The recovered maleic anhydride may then be used in a variety of applications, for example, as a chemical intermediate in the synthesis of fumaric and tartaric acid and in certain agrochemical chemicals, dye intermediates and pharmaceuticals. It may also be used as a co-monomer for polyester and alkyd resins, as an ingredient in the manufacture of surface coatings, lubricant additives, plasticizers and as a preservative in oils and fats.

EXAMPLES

VPO catalysts in both conventional shape (i.e. rounded trilobe) and inventive shape (i.e. rounded trilobe with hollow core) were prepared from vanadium pyrophosphate powder as described below. Catalyst physical properties were obtained and performance was then determined using commercial size single tube reactors.

In general, a VPO catalyst precursor powder was made according to the disclosure of U.S. Pat. Nos. 5,185,455 and 5,275,996, the entire contents of which are herein incorporated by reference. The VPO catalyst precursor powder was then blended to contain approximately four (4.0) weight % graphite and compressed on a Stokes 512 Rotary Tableting machine equipped with appropriate dies and punches to produce a 1.27 cm long cylinder slug with a tablet density between 1.0-2.0 g/cm³. The 1.27 cm slug was then ground to produce a tablet feed in the size range of from 18 mesh [U.S. Standard Sieve Size, 1.00 millimeter (mm)] to 30 mesh (600 microns, µm) and was then fed into the tableting machine equipped with appropriate dies and punches to produce the shaped catalyst of interest.

Each of the shaped catalysts produced were then activated by the following steps. The shaped catalysts were first placed onto a tray with approximately 40% open area. The tray was then transferred to an air-purged programmable box oven at 200°-350° C. Thereafter, the tray of shaped catalysts was removed from the oven, cooled and then transferred to a box oven purged with nitrogen gas. The tray was then heated to approximately 200°-350° C. at which temperature the atmosphere in the oven was then changed to a mixture of approximately 20-70% by volume nitrogen and 20-70% by volume steam. The temperature was then raised over a period of from one hour to two hours to approximately 400°-500° C. and maintained for approximately six hours. The tray of shaped catalysts was then allowed to cool to room temperature (approximately 20°-50° C.) while the oven was purged with dry nitrogen or air. The shaped catalysts were then charged to the reactor. In so doing, the amount of catalyst charged to the reactor was a direct result of the tube filling characteristics of the shaped catalyst of interest. The shaped catalyst was run in both a micro-reactor and commercial size single tube reactor for ~350 hours at the standardized conditions of 2.05 mol % n-butane, 2.4% steam, 26 psig inlet pressure, and 1820 GHSV and at control 85% conversion in order to test steady state yield.

Example 1. VPO catalyst precursor powder was generally prepared as follows. A 5-liter flask fitted with a paddle stirrer, a thermometer, a heating mantle, and a reflux condenser was charged with isobutyl alcohol (2591 grams), oxalic acid (108 grams), and $V_2O_5$ (300 grams). Phosphoric acid (105.7% $H_3PO_4$; 361 grams) was thereafter added to the flask. The resulting mixture was then refluxed for about 12 hours, yielding a bright blue reaction mixture. Approximately one-fourth of the alcohol solvent was then stripped from this mixture, after which the residue in the reactor was cooled and half of the remaining solvent was decanted to produce a concentrated slurry. The concentrated slurry was then quantitatively transferred to a flat dish and dried at a temperature between 110° C. and 150° C. in nitrogen. The dried material was then further dried by heating in nitrogen/air at 250° C. to 260° C. for several hours to yield a gray-black VPO catalyst precursor powder. The VPO precursor powder prepared in this manner had a P/V ratio of 1.08±0.05.

The above prepared VPO precursor powder was then blended to contain approximately four (4.0) weight % graphite and compressed on a Stokes 512 Rotary Tableting machine equipped with appropriate dies and punches to produce a shaped catalyst structure (1.27 cm cylinders with a tablet density of 1.30-1.50 g/cm³). The 1.27 cm slugs were ground to produce a tablet feed powder in the size range of from 18 mesh [U.S. Standard Sieve Size, 1.00 millimeter (mm)] to 30 mesh (600 microns) and fed into the tableting machine equipped with 5/16" diameter rounded trilobe dies and punches to produce the shaped catalyst bodies.

The shaped catalyst bodies were then activated by processing in a box oven with the following protocol of temperature and gas composition. The shaped catalyst bodies were heated in air or nitrogen to 250° C. as a starting temperature for ramp heating. An oven heat-up was then conducted from 250° C. to 425° C. at a controlled rate of 4° C. per minute in an atmosphere of 50% air and 50% steam. The temperature of the shaped catalyst bodies was thereafter maintained at 425° C. for one hour under the aforesaid 50% air/50% steam atmosphere. After this one-hour hold, the gas atmosphere was changed to 50% nitrogen and 50% steam and the temperature of the shaped catalyst bodies was maintained at 425° C. for an additional six hours, after which they were cooled. Activated 5/16" rounded trilobe VPO catalysts were thus obtained.

Example 2. VPO catalyst precursor powder was prepared in the same manner as described in Example 1. Using a Stokes 512 rotary tableting machine equipped with designed 5/16" cored trilobe dyes and punches with a center hole, the above prepared VPO precursor powder was formed into a cored 5/16" rounded trilobe catalyst. The cored shaped catalyst bodies were then processed in a box oven using the same protocol of temperature and gas composition as described above to obtain an activated 5/16" cored rounded trilobe VPO catalysts.

Example 3. VPO catalyst precursor powder was prepared in the same manner as described in Example 1. Using a Stokes 512 rotary tableting machine equipped with designed 9/32" conventional rounded trilobe dyes and punches, the above prepared VPO precursor powder was formed into a 9/32" rounded trilobe catalyst bodies. The shaped catalyst bodies were then processed in a box oven using the same protocol of temperature and gas composition as described above to obtain activated 9/32" rounded trilobe VPO catalysts.

Example 4. VPO catalyst precursor powder was prepared in the same manner as described in Example 1. Using a Stokes 512 rotary tableting machine equipped with designed 9/32" cored trilobe dyes and punches with a center hole, the above prepared VPO precursor powder was formed into cored 9/32" rounded trilobe catalyst bodies. The shaped catalyst bodies were then processed in a box oven using the same protocol of temperature and gas composition as described above to obtain activated 9/32" cored rounded trilobe VPO catalyst bodies.

Example 5. The catalysts obtained Example 1 were further subjected to an organic solvent treatment. The catalysts (conventional 5/16" round trilobe) were blended, and then loaded into a 4" diameter glass column to form a total catalyst bed height of about 33 cm. The column skin was then heated by a heating element coiled around the glass column. Preheated ethylene glycol (EG, Aldrich, 99.8%) was then circulated through the catalyst bed from the top using a pump and the temperature of the catalyst bed was controlled at about 100° C.±20° C. Ethylene glycol circulation was maintained for 4 hours at a rate of about 140 ml/min.

After 4 hours of circulation, the pump was stopped and the ethylene glycol that remained in the column was drained out. Preheated nitrogen was then blown down from the top of the column to remove any remaining ethylene glycol. The catalyst bed temperature was then gradually ramped up to 350° C. and held there for 5 hours to dry the catalyst bed. After 5 hours of drying, all heating sources were shut down and the catalyst bed was allowed to gradually cool overnight. The dried catalyst bed that was obtained comprised solvent treated 5/16" conventional rounded trilobe catalysts.

Example 6. This example demonstrates an inventive catalyst shape further treated with an organic solvent. The catalysts that were obtained in Example 2 were subjected to the same organic solvent treatment process described in Example 5. The dried catalyst bed that was obtained comprised solvent treated 5/16" cored rounded trilobe catalysts.

Example 7. The catalysts that were obtained in Example 3 were subjected to the same organic solvent treatment process described in Example 5. The dried catalyst bed that was obtained comprised solvent treated 9/32" conventional rounded trilobe catalysts.

Example 8. The catalysts that were obtained in Example 4 were subjected to the same organic solvent treatment process described in Example 5. The dried catalyst bed that was obtained comprised solvent treated 9/32" cored rounded trilobe catalysts.

Example 9. VPO precursor powder was prepared in the same manner as described in Example 1. Using a Stokes 512 rotary tableting machine equipped with designed ¼" conventional rounded trilobe dyes and punches, the above prepared VPO precursor powder was formed into ¼" rounded trilobe catalyst bodies. These catalyst bodies were then processed in a box oven with the same protocol of temperature and gas composition to obtain activated ¼" rounded trilobe VPO catalysts.

Example 10. The catalysts obtained in example 9 were subjected to the same organic solvent treatment process in the manner described in Example 5. The dried catalyst bed that was obtained comprised solvent treated ¼" rounded trilobe catalysts.

Example 11. VPO precursor powder was prepared in the same manner as described in Example 1. Using a Stokes 512 rotary tableting machine equipped with designed ¼" conventional regular trilobe dies and punches with a center hole, the above prepared VPO precursor powder was formed into ¼" cored trilobe catalyst bodies. These catalyst bodies were then processed in a box oven using the same protocol of temperature and gas composition described above to obtain activated ¼" cored rounded trilobe VPO catalysts.

Physical properties of selected different sized and shaped catalysts were tested and the results are summarized in Table 1. As shown below, the cored shaped catalysts according to the present disclosure can provide more surface area, more pore volume, as well as higher crush strength.

TABLE 1

Physical Properties For Different Sized And Shaped Catalysts

| Example | | Size & Shape* | BET Surf. Area ($m^2/g$) | Pore Volume ($cm^3/g$) | Crush Strength (N) |
|---|---|---|---|---|---|
| 1 | Activated | 5/16" RT | 20.3 | 0.218 | 16.6 |
| 2 | catalyst | 5/16" CRT | 28.9 | 0.240 | 21.1 |
| 3 | | 9/32" RT | 22.8 | 0.203 | 19.5 |
| 4 | | 9/32" CRT | 25.5 | 0.338 | 38.0 |
| 5 | Solvent | 5/16" RT | 30.9 | 0.396 | 7.9 |
| 6 | treated | 5/16" CRT | 25.5 | 0.407 | 11.6 |
| 7 | catalyst | 9/32" RT | 32.2 | 0.313 | 10.4 |
| 8 | | 9/32" CRT | 34.6 | 0.391 | 17.4 |

RT = rounded trilobe; CRT = cored rounded trilobe

Commercial-Size Reactor Performance Test Description

Catalysts prepared in the manner described in Examples 1-11 were tested for efficiency in terms of reaction yield of maleic anhydride, pressure drop, and salt bath temperature. In each test, the catalyst bodies were charged to a 21.0 mm inner diameter by 6000 mm long fixed bed tubular reactor. A butane oxidation reaction was then conducted for several hundred hours of on-stream time. The general test conditions were: 2.05% Butane, 2.4% Steam, 8-10 ppm TMP, ~85% Conversion, 1820 GHSV, 26 psig inlet, 224 inches catalyst bed (packed between 6" alumina inerts on both ends of bed), average time ~350 hrs on line.

In a test series designated A, a standard ¼" trilobe shape catalyst was tested for 17 trials: the average packing density was 0.55 kg/L, average molar yield was 57.9%, average salt bath temperature was 416.5° C., and average pressure drop was 7.7 psig.

In a test series designated B1, multiple tests were conducted for a ¼" rounded trilobe catalyst shape: the average packing density was 0.62 kg/L, average molar yield was 58.4%, average salt bath temperature was 412.1° C., and average pressure drop was 9.2 psig.

In a series designated B2, multiple tests were conducted for a ¼" rounded trilobe catalyst shape: the average packing density was 0.55 kg/L, average molar yield was 60.0%, average salt bath temperature was 409.3° C., and average pressure drop was 10.2 psig.

In a test series designated C1, multiple tests were conducted for a 9/32" rounded trilobe catalyst shape: the average packing density was 0.59 kg/L, average molar yield was 56.6%, average salt bath temperature was 412.1° C., and average pressure drop was 8.0 psig.

In a test series designated C2, multiple tests were conducted for a 9/32" rounded trilobe catalyst shape: the average packing density was 0.52 kg/L, average molar yield was 58.9%, average salt bath temperature was 413.7° C., and average pressure drop was 8.4 psig.

In a test series designated D1, multiple tests were conducted for a 5/16" rounded trilobe catalyst shape: the average packing density was 0.54 kg/L, average molar yield was 56.9%, average salt bath temperature was 417.2° C., and average pressure drop was 6.0 psig.

In a test series designated D2, multiple tests were conducted for a 5/16" rounded trilobe catalyst shape: the average packing density was 0.52 kg/L, average molar yield was 58.0%, average salt bath temperature was 415.7° C., and average pressure drop was 7.1 psig.

In a series designated E1, multiple tests were conducted for a 9/32" cored rounded trilobe catalyst shape: the average packing density was 0.55 kg/L, average molar yield was 57.7%, average salt bath temperature was 413.0° C., and average pressure drop was 5.2 psig.

In a series designated E2, multiple tests were conducted for a 9/32" rounded trilobe catalyst shape: the average packing density was 0.52 kg/L, average molar yield was 59.5%, average salt bath temperature was 410.9° C., and average pressure drop was 5.5 psig.

For each test series, the catalyst was brought on-stream at low butane concentration which was then increased to 2.05 mole % butane over the first several hundred hours of operation. Performance test results for activated catalysts in different shapes are summarized below in Table 2 while performance test for solvent treated catalyst of different shapes are summarized in Table 3.

TABLE 2

Single Tube Reactor Test for Activated Catalysts

| Test ID | Catalyst Type (Activated) | Catalyst Packing Density | ΔBCY vs Standard | ΔSBT vs Standard | Average ΔP psig |
|---|---|---|---|---|---|
| A | ¼" TL (Standard) | 0.55 | | | 7.7 |
| B1 | ¼" RT | 0.62 | 0.5 | (4.4) | 9.2 |
| C1 | 9/32" RT | 0.59 | (1.3) | (4.4) | 8.0 |
| D1 | 5/16" RT | 0.54 | (0.9) | 0.7 | 6.0 |
| E1 | 9/32" CRT | 0.55 | (0.2) | (3.5) | 5.2 |

TL = trilobe; RT = rounded trilobe; CRT = cored rounded trilobe

TABLE 3

Single Tube Reactor Test For Solvent Treated Catalysts

| Test ID | Catalyst Type (Solvent Treated) | Catalyst Packing Density | ΔBCY vs Standard | ΔSBT vs Standard | Average ΔP psig |
|---|---|---|---|---|---|
| A | ¼" TL (Standard) | 0.55 | | | 7.7 |
| B2 | ¼" RT | 0.55 | 2.1 | (7.3) | 10.7 |
| C2 | 9/32" RT | 0.52 | 1.0 | (2.8) | 8.4 |
| D2 | 5/16" RT | 0.52 | 0.1 | (0.9) | 7.1 |
| E2 | 9/32" CRT | 0.52 | 1.7 | (5.6) | 5.5 |

TL = trilobe; RT = rounded trilobe; CRT = cored rounded trilobe

As shown above in Table 2, when tested under the same conditions, it can be seen that activated catalyst size influences performance. For instance, a smaller catalyst size produced a higher yield, but a correspondingly higher pressure drop in the reactor (which can be an obstacle during commercial operations). The shape of the catalyst was also shown to be an important factor for catalytic effects during the performance test. For the activated catalyst tests, it can be seen that the performance for 9/32" and 5/16" rounded trilobe catalysts (C1 and D1) was lower than that for ¼" standard catalyst (A). The pressure drop for catalyst C1 was also higher than that for catalyst A. While catalyst B1 exhibited a slightly higher performance as compared to catalyst A, the pressure drop for catalyst B1 was much higher than that for catalyst A. In comparison, the inventive cored rounded trilobe catalyst E1 demonstrated comparable yield performance compared to that for standard catalyst A, however, the pressure drop for catalyst E1 was significantly lower than that for catalyst A (as well as that for the other conventional rounded trilobe shaped catalysts). Catalyst E1 also exhibited higher activity (lower salt bath) than that for standard catalyst A which may lead to a longer lifetime for catalyst E1.

For the solvent treated catalyst tests, although catalysts B2 and C2 exhibited a higher performance as compared to catalyst A, the pressure drops for these catalysts were again much higher than that for catalyst A. For catalyst D2, neither a performance nor pressure drop benefit was observed. However, the inventive shaped catalysts E2 not only exhibited an improvement in yield (about 1.7 above that for catalyst A), it also demonstrated a much lower pressure drop than that for any other of the catalysts tested. In addition, catalyst E2 exhibited a higher surface area, pore volume, and side crush strength as compared to the conventional shaped catalyst.

In summary, the rounded trilobe shaped catalysts lacked either an improved performance and/or pressure drop as compared to the standard trilobe. However, the inventive shaped catalysts (cored trilobe) showed to have an advantage over both the standard trilobe shape (i.e. a similar yield but much lower ΔP if not solvent treated, but ~1.7 better yield plus a lower ΔP when solvent treated) an rounded trilobe shape.

In addition, the longest diffusion paths for inventive shaped catalysts and similarly shaped catalyst without a hollow core were determined to be:

| Example | Longest Diffusion Path for 5/16" Outer Diameter | Longest Diffusion Path for 9/32" Outer Diameter | Longest Diffusion Path for ¼" Outer Diameter |
|---|---|---|---|
| Shaped Catalyst with a hollow core | 0.119 | 0.107 | 0.095 |

-continued

| Example | Longest Diffusion Path for 5/16" Outer Diameter | Longest Diffusion Path for 9/32" Outer Diameter | Longest Diffusion Path for 1/4" Outer Diameter |
|---|---|---|---|
| Shaped Catalyst without a hollow core | 0.156 | 0.141 | 0.125 |

As shown above, the inventive shaped catalysts were surprisingly found to have about a 24% less longest diffusion path than the longest diffusion path for a similar shaped lobed catalyst but without a hollow core.

While the foregoing is directed to various aspects of the present disclosure, other and further aspects of the disclosure may be devised without departing from the basic scope thereof, and the scope thereof is determined by the claims that follow.

The invention claimed is:

1. A shaped catalyst for preparing maleic anhydride comprising:
    a) a catalytic material comprising mixed oxides of vanadium and phosphorus and;
    b) a hollow core; and
    c) a first end, a second end and a wall disposed between the first end and the second end, the wall comprising a height and n crenellations running along the height of the wall to form n lobes wherein each lobe has a corner defined by a lobe radius and n is 3, 4 or 5.

2. The shaped catalyst according to claim 1 wherein the crenellations are circular arcs.

3. The shaped catalyst according to claim 2 wherein the wall has three crenellations to form three lobes.

4. The shaped catalyst according to claim 2 wherein the wall has a height ranging from 1 mm to 20 mm.

5. The shaped catalyst according to claim 2 wherein the first end and second end have a diameter ranging from 5 mm to 9 mm.

6. The shaped catalyst according to claim 2 wherein the hollow core has a diameter ranging from 0.5 mm to 4 mm.

7. The shaped catalyst according to claim 2 wherein an inner crenellation feature connecting innermost points of the crenellations has a diameter ranging from 2 mm to 4.5 mm.

8. The shaped catalyst according to claim 2 wherein the lobe radius ranges from 0.375 mm to 0.75 mm.

9. The shaped catalyst according to claim 2 wherein an outer crenellation feature connecting the innermost points and projecting edges of a crenellation has a diameter ranging from 2 mm to 3.5.

10. The shaped catalyst according to claim 2 wherein the shaped catalyst has a three points of contact distance ranging between 4 mm and 8 mm.

11. The shaped catalyst according to claim 10 wherein the shaped catalyst has a two points of contact distance ranging between 5 mm and 10 mm.

12. The shaped catalyst according to claim 5 wherein a ratio of a diameter of the hollow core to the diameter for the first end and the second end is between 0.15 and 0.3.

13. The shaped catalyst according to claim 7 wherein a ratio of a diameter of the hollow core to the diameter of the inner crenellation feature ranges between 0.4 and 0.6.

14. The shaped catalyst according to claim 8 wherein a ratio of a diameter of the hollow core to the lobe radius ranges between 2.8 and 3.2.

15. The shaped catalyst according to claim 2 further wherein the shaped catalyst has a side crush strength of greater than 10 lbs.

16. A method for preparing a shaped catalyst comprising reacting a vanadium-containing compound and a phosphorus-containing compound in an alcoholic medium to produce a VPO catalyst precursor, shaping the VPO catalyst precursor to form the shaped catalyst and activating the shaped catalyst by calcination wherein the shaped catalyst comprises
    a) a catalytic material comprising mixed oxides of vanadium and phosphorus and;
    b) a hollow core; and
    c) a first end, a second end and a wall disposed between the first end and the second end, the wall comprising a height and n crenellations running along the height of the wall to form n lobes wherein each lobe has a corner defined by a lobe radius and n is 3, 4 or 5.

17. The method according to claim 16 wherein the VPO catalyst precursor is shaped by pressing or compacting in a mold.

18. The method of claim 17 wherein the shaped catalyst is subjected to a series of contactings with an organic solvent or a mixture of organic solvents after calcination.

19. A process for preparing maleic anhydride comprising reacting a hydrocarbon having at least four carbons in a straight chain or cyclic ring with a molecular oxygen-containing gas in the presence of a shaped catalyst according to claim 1.

20. The process according to claim 19 wherein the hydrocarbon having at least four carbons in a straight chain or cyclic ring is selected from n-butane, 1-butene, 2-butene, benzene and a mixture thereof.

* * * * *